(12) United States Patent
Nakayama

(10) Patent No.: US 6,555,312 B1
(45) Date of Patent: Apr. 29, 2003

(54) METHOD FOR DETECTING BACTERIA WITH BACTERIAPHAGE

(75) Inventor: Hiroshi Nakayama, Osaka (JP)

(73) Assignee: Matsushita Electric Industrial Co., Ltd., Osaka (JP)

( * ) Notice: Subject to any disclaimer, the term of this patent is extended or adjusted under 35 U.S.C. 154(b) by 0 days.

(21) Appl. No.: 09/510,072

(22) Filed: Feb. 22, 2000

(30) Foreign Application Priority Data

Feb. 22, 1999 (JP) ............................................ 11-043959

(51) Int. Cl.$^7$ ................................................ C12Q 1/70
(52) U.S. Cl. ............................ 435/5; 435/7.32; 435/6; 435/4; 435/189; 435/325; 530/350
(58) Field of Search ........................... 435/189, 5, 7.32, 435/6, 4, 325; 530/350

(56) References Cited

U.S. PATENT DOCUMENTS

| | | | | |
|---|---|---|---|---|
| 3,819,482 A | * | 6/1974 | Vidaver et al. | 195/28 N |
| 4,273,660 A | * | 6/1981 | Beitzel | 210/760 |
| 4,861,709 A | * | 8/1989 | Ulitzur et al. | 435/6 |
| 5,162,227 A | * | 11/1992 | Cormier | 435/252.33 |
| 5,491,084 A | * | 2/1996 | Chalfie | 435/189 |
| 5,766,941 A | * | 6/1998 | Cormier et al. | 530/324 |
| 5,824,468 A | * | 10/1998 | Sherer et al. | 435/5 |
| 5,914,240 A | * | 6/1999 | Sanders | 435/7.32 |
| 5,998,204 A | * | 12/1999 | Tsien et al. | 435/325 |
| 6,090,541 A | * | 7/2000 | Wicks et al. | 435/5 |
| 6,090,542 A | * | 7/2000 | Baeuerle et al. | 435/6 |
| 6,146,826 A | * | 11/2000 | Chalfie et al. | 435/6 |
| 6,172,188 B1 | * | 1/2001 | Thastrup et al. | 530/350 |
| 6,190,856 B1 | * | 2/2001 | Li | 435/4 |
| 6,197,928 B1 | * | 3/2001 | Tsien et al. | 530/350 |
| 6,203,986 B1 | * | 3/2001 | Singer et al. | 435/6 |
| 6,247,995 B1 | * | 6/2001 | Bryan | 446/473 |
| 6,284,496 B1 | * | 9/2001 | Litman et al. | 435/91.2 |

FOREIGN PATENT DOCUMENTS

| | | | |
|---|---|---|---|
| JP | 11-32761 | 2/1999 | |
| JP | 11-266863 | 10/1999 | |
| JP | 11-318499 | 11/1999 | |
| WO | 85/04189 | 9/1985 | |
| WO | 95/07463 | * 3/1995 | ......... G01N/33/53 |
| WO | 98/13515 | 4/1998 | |

OTHER PUBLICATIONS

European Search Report Application No. EP 00 10 3604 dated Jun. 27, 2000.

(List continued on next page.)

Primary Examiner—Lynette R. F. Smith
Assistant Examiner—Ginny Allen Portner
(74) Attorney, Agent, or Firm—Renner, Otto, Boisselle & Sklar, LLP

(57) ABSTRACT

A method for detecting a bacterium for measurement, including the steps of: allowing a bacteriophage to bind to the bacterium, the bacteriophage being capable of specifically binding to the bacterium and growing in the bacterium, whereby a gene within the bacteriophage which expresses a light-emission protein is introduced into the bacterium so that a protein is produced within the bacterium as a product of the gene; and providing an external factor in a non-invasive manner from outside of the bacterium, thereby causing only the actually-present bacterium to emit light in a specific manner.

5 Claims, 1 Drawing Sheet

OTHER PUBLICATIONS

Hennes, K.P. et al.; "Fluorescently Labeled Virus Probes Show That Natural Virus Populations Can Control The Structure of Marine Microbial Communities"; *Appl. Environ. Microbol.*, vol. 61, No. 10, 1995; pp. 3623–3627.

Hatfull, GF et al, Molecular Microbiology, vol. 7(3), Feb. 1993, pp. 395–405 (abstract only).*

He, XQ et al, Journal of Clinical Microbiology, vol. 30(3), Mar. 1992, pp. 590–594 (abstract only).*

Jensen, EC et al, Applied and Environmental Microbiology, vol. 64(2), pp. 575–580, Feb. 1998.*

Nadeau, K et al, Journal of Biological Chemistry, vol. 268(2), pp. 1479–1487, Jan. 15, 1993 (abstract only).*

Niswender,KD et al, Journal of Microscopy, vol. 180(2), pp. 109–116, Nov. 1995.*

Sarkis, GJ et al, Molecular Microbiology, vol. 15(6), pp. 1055–1067, Mar. 1995 (abstract only).*

Ulitzer, S et al, Identification of bacteria and their antibotic susceptibility by the aid of luciferase genes carrying bacteriophage. Program and abstracts Second International Marine Biotechnology Conference, p. 60, 1991, Oct. 13–16 (abstract onl.*

Chalfie, M et al, Science, vol. 263, Feb. 11, 1994, pp. 802–805.*

Cubitt, AB et al, TIBS, vol. 20, Nov. 1995, pp. 448–455.*

Valdivia, RH et al, Gene, vol. 173, pp. 47–55, 1996.*

* cited by examiner

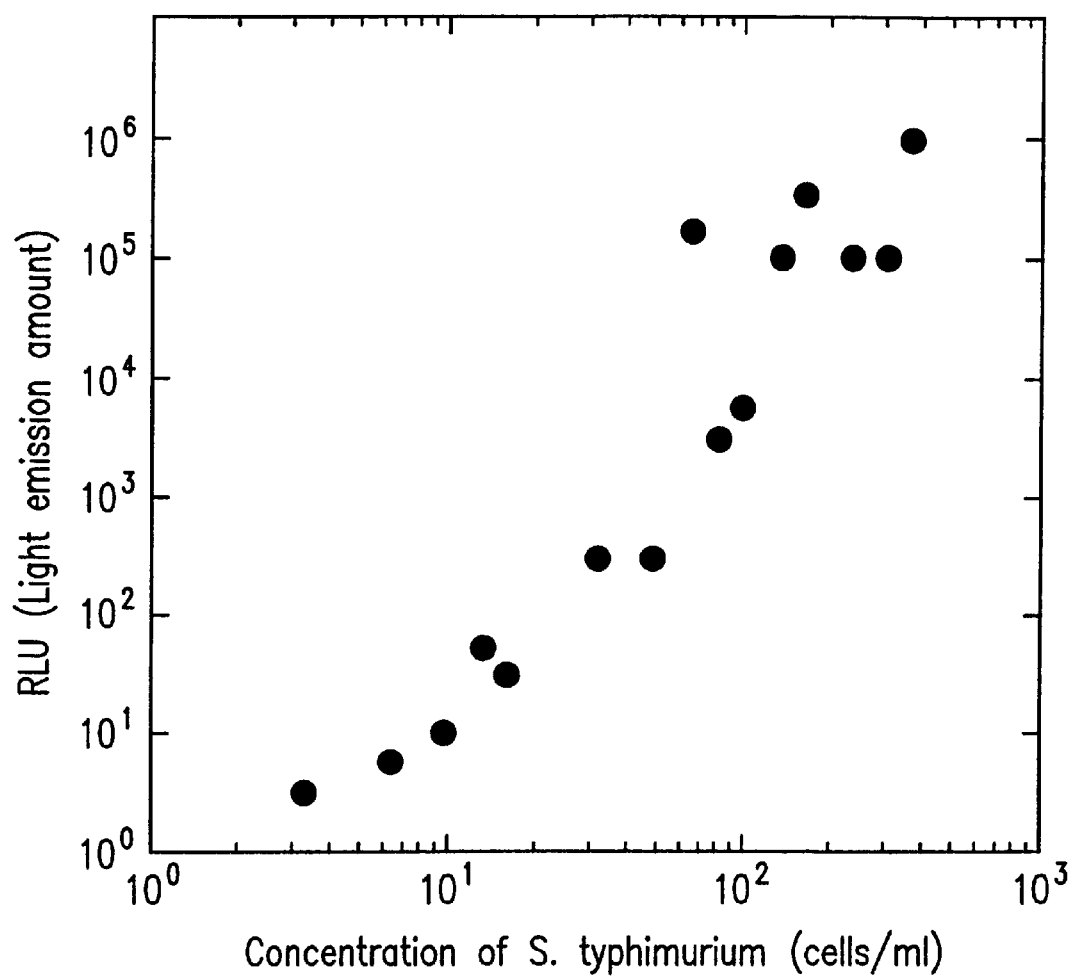
FIGURE

METHOD FOR DETECTING BACTERIA WITH BACTERIAPHAGE

BACKGROUND OF THE INVENTION

1. Field of the Invention

The present invention relates to a method for detecting or identifying a bacterium in a specific and yet easy manner by employing a bacteriophage into which a light-emission gene is inserted. The method of the present invention can be utilized as a means for measuring or detecting a bacterium, and is particularly useful in fields of environmental, food, and medical applications.

2. Description of the Related Art

Numerous tests exist for determining the presence and identifying the type of bacterium. Most of these methods involve culturing a sample containing an unidentified bacterium in a medium (which may be of a variety of types) and thereafter observing the culturological characteristics, morphological characteristics, biological characteristics, sensitivity with respect to antibiotics, absorption of various colorants, serological characteristics, etc., of the unidentified bacterium. However, such conventional methods require selection of media and the like in order to effect the selective growth of a relevant bacterium while preventing the growth of irrelevant bacteria. Due to such requirements, conventional methods may take a considerable amount of time for identifying a relevant organic body (bacterium) after the isolation of the bacterium.

In order to solve the aforementioned problems, methods have been developed which detect the presence of a bacteria by introducing into a bacterium a foreign gene for producing a protein that expresses a detectable function, and allowing the introduced gene to be expressed so that the bacterium can be detected based on the expressed function.

Conventional bacterium detection methods which utilize biological light emission typically attain light emission by using an enzyme known as luciferase and its substrate, luciferin, to permit a reaction therebetween in the presence of adenosine triphosphate (ATP) of bacterial origin. According to such conventional methods, a reaction solution in which luciferase and luciferin are mixed is prepared; after a sample (e.g., meat) is crushed, the reaction solution is added to the crushed matter or an extract obtained after crushing. If the sample contains a bacterium, light emission can be observed because the adenosine triphosphate (ATP) which was contained in the bacterium will leak out of the bacterium during the crushing, so that the action of the leaking ATP allows a light emission reaction to occur in the reaction solution. The bacterium in question can be detected by detecting the intensity of light emission (see Japanese Laid-Open Publication No. 5-30997). However, this measurement system may also measure any ATP that is derived from cells other than the bacterium which is suspected to be present in the sample. As a result, there are problems of misdetection possibilities and substantial degradation in the sensitivity.

On the other hand, methods are also known which involve a step of introducing a gene which express luciferase into a vector, e.g., a bacteriophage, and a step of infecting a bacterium with this virus. According to this method, after the introduction of the gene, luciferin is introduced from outside of the bacterium in an invasive manner, and light emission is effected through an enzymatic reaction utilizing the ATP within the cell. The bacterium in question can be detected by detecting the intensity of light emission (see Japanese Publication for Opposition No. 6-34757). This technique will inevitably destroy all or some of the cells under examination because the introduction of luciferin is achieved by a method which is invasive to the bacterial cells. Hence, this technique is not exactly satisfactory in terms of misdetection possibilities and degradation in sensitivity.

SUMMARY OF THE INVENTION

According to the present invention, there is provided a method for detecting a bacterium for measurement, including the steps of: allowing a bacteriophage to bind to the bacterium, the bacteriophage being capable of specifically binding to the bacterium and growing in the bacterium, whereby a gene within the bacteriophage which expresses a light-emission protein is introduced into the bacterium so that a protein is produced within the bacterium as a product of the gene; and providing an external factor in a non-invasive manner from outside of the bacterium, thereby causing only the actually-present bacterium to emit light in a specific manner.

In one embodiment of the invention, the bacterium is selected from a group including: Rhodospirillaceae, Chromatiaceae, Chlorobiaceae, Myxococcaceae, Archangiaceae, Cystobacteraceae, Polyangiaceae, Cytophagaceae, Beggiatoaceae, Simonsiellacea, Leucotrichaceae, Achromatiaceae, Pelonemataceae, Sprirochaetaceae, Spirillaceae, Pseudomonadaceae, Azotobacteraceae, Rhizobiaceae, Methylomonadaceae, Halobacteriaceae, Enterobacteriaceae, Vibrionaceae, Bacteroidacea, Neisseriaceae, Veillonellaceae, Organisms oxidizing ammonia or nitrite, Organisms metabolizing sulfur and sulfur compounds, Organisms depositing iron and/or manganese oxides, Siderocapsaceae, Methanobacteriaceae, Aerobic and/or facultatively anaerobic Micrococcaceae, Streptococcaceae, Anaerobic Peptococcaceae, Bacillaceae, Lactobacillaceae, Coryneform group of bacteria, Propionibacteriaceae, Actinomycetaceae, Mycobacteriaceae, Frankiaceae, Actinoplanaceae, Dermatophilaceae, Nocardiaceae, Streptomycetaceae, Micromonosporaceae, Rickettsiaceae, Bartonellaceae, Anaplasmataceae, Chlamydiaceae, Mycoplasmataceae, and Acholeplasmataceae In another embodiment of the invention, the bacteriophage is selected from a group including T4, P2, T2, T7, λ, MV-L2, PRD1, PM2, MV-L1, ΦX174, fd, MS2, Φ6, FELIX01, and G47.

In still another embodiment of the invention, the light-emission protein is green-fluorescent protein (GFP) or blue-fluorescent protein (BFP).

In still another embodiment of the invention, the external factor is light.

According to the present invention, there is also provided a method for identifying a bacterium present in a sample, including the steps of: allowing a bacteriophage to bind to the bacterium, the bacteriophage being capable of specifically binding to the bacterium and growing in the bacterium, whereby a gene within the bacteriophage which expresses a light-emission protein is introduced into the bacterium so that a protein is produced within the bacterium as a product of the gene; and providing an external factor in a non-invasive manner from outside of the bacterium, thereby causing only the actually-present bacterium to emit light in a specific manner.

According to the method of the present invention, a light-emission reaction can be effected without crushing or otherwise damaging a bacterium, such that the light-emission reaction occurs only within the bacterium.

Accordingly, a bacterial measurement is achieved which is substantially free of misdetection possibilities and which provides high sensitivity. As a result, the method according to the present invention enables detection or identification of a bacterium in a quick and specific manner, without requiring complicated processes.

In particular, by adopting a protein which does not require any substrate for light emission (e.g., green-fluorescent protein) as a light-emission protein, it becomes possible to omit invasive introduction of an external factor from outside of the bacterium, a problematic step which is associated with conventional methods utilizing a luciferase-luciferin system.

Thus, the invention described herein makes possible the advantage of providing a method for detecting or identifying a bacterium species within a sample, in a specific, highly-sensitive, quick and secure manner, the method involving providing an external factor for the bacterial cell in a non-invasive manner so that the external factor induces a light-emission reaction.

This and other advantages of the present invention will become apparent to those skilled in the art upon reading and understanding the following detailed description with reference to the accompanying figures.

BRIEF DESCRIPTION OF THE DRAWINGS

The FIG. 1 is a graph describing detection results for *Salmonellae typhimurium*.

DESCRIPTION OF THE PREFERRED EMBODIMENTS

The method for detecting or identifying a bacterium for measurement according to the present invention involves: (binding step) allowing a bacteriophage (hereinafter also simply referred to as a "phage") to bind to a bacterium so as to cause a gene within the phage for expressing a light-emission protein to be introduced into the bacterium; and (light-emission srep) providing an external factor from outside of the bacterium to cause only the interested bacterium to emit light in a specific manner. Specifically, in the binding step, a bacterium is infected with a bacteriophage which includes a gene coding for a light-emission protein. The binding step may further involve a step of allowing the phage used for infection to grow within in the host cell, whereby the gene coding for the light-emission protein can be amplified. The phage used for infection can grow usually up to at least about $10^2$ to about $10^4$ phage particles/bacterial cell, up to a level slightly below where the destruction of the host bacterial cell would occur. Accordingly, the gene coding for the light-emission protein can be amplified by at least about $10^2$ to about $10^4$ times. The bacterium of interest can be detected in the ensuing light-emission step, where the light-emission protein which is produced from this gene is allowed to emit light responsive to the application of an external factor.

Examples of bacteria for measurement which can be measured by the method according to the present invention, include, without limitation, the following bacteria: Rhodospirillaceae, Chromatiaceae, Chlorobiaceae, Myxococcaceae, Archangiaceae, Cystobacteraceae, Polyangiaceae, Cytophagaceae, Beggiatoaceae, Simonsiellaceae, Leucotrichaceae, Achromatiaceae, Pelonemataceae, Spirochaetaceae, Sprillaceae, Pseudomonadaceae, Azotobacteraceae, Rhizobiaceae, Methylomonadaceae, Halobacteriaceae, Enterobacteriaceae, Vibrionaceae, Bacteroidaceae, Neisseriaceae, Veillonellaceae, Organisms oxidizing ammonia or nitrite, Organisms metabolizing sulfur and sulfur compounds, Organisms depositing iron and/or manganese oxides, Siderocapsaceae, Methanobacteriaceae, Aerobic and/or facultatively anaerobic) Micrococcaceae, Streptococcaceae, Anaerobic Peptococcaceae, Bacillaceae, Lactobacillaceae, Coryneform group of bacteria, Propionibacteriaceae, Actinomycetaceae, Mycobacteriaceae, Frankiaceae, Actinoplanaceae, Dermatophilaceae, Nocardiaceae, Streptomycetaceae, Micromonosporaceae, Rickettsiaceae, Bartonellaceae, Anaplasmataceae, Chlamydiaceae, Mycoplasmataceae, and Acholeplasmataceae. Thus, according to the present invention, any bacteria of the so-called phage type, which are susceptible to infection by phages, can be used as the bacteria for measurement.

When practicing the present invention, it is desirable to select a phage having properties such that they specifically bind to a selected bacterium for measurement (as exemplified above) and grow therein. Phages which specifically bind to particular bacteria for measurement, i.e., specific phage-bacterium combinations, are known in the art.

Useful phages are available from, for example, the American Type Culture Collection (ATCC). The details of available strains are disclosed in "Catalogue of Bacteria & Bacteriophages" published by the ATCC.

Examples of naturally occurring bacteriophages which are available include, without limitation, the following bacteriophages: T4, P2, T2, T7, λ, MV-L2, PRD1, PM2, MV-L1, ΦX174, fd, MS2, Φ6, FELIX01, and G47. For each of these phages, a bacterium is known to specifically bind to the phage. For example, T4, P2, T2, T7, λ, ΦX174, and MS2 phages are exemplary phages which are desirable for the detection of Enterobacteriaceae, e.g., *E. coli*. Φ6 and PM2 phages are exemplary phages which are desirable for the detection of Pseudomonadaceae. FELIX01 phage is an exemplary phage which is desirable for the detection of salmonellae.

In addition to the known deposited phages, desirable phages can be obtained by isolating the phages from an appropriate environment. As used herein, an "appropriate environment" is preferably an environment in which a bacterium for measurement itself can be found. Techniques for isolating phages are known in the art (see, for example, Loessner and Busse, Applied and Environmental Microbiology, vol. 56, pp. 1912–1918 (1990), and "Bacteriophages" Interscience Inc., pp. 447–455 (1959)).

It is possible to modify such phages or other viruses so as to become capable of specifically binding to a bacterium for measurement and growing therein. For example, phages (e.g., EMBL3, EMBL4) which have been improved for cloning are commercially available. Techniques for modifying phages or other viruses by using recombinant DNA technology are known to those skilled in the art.

Heterogeneous DNA can be introduced into a vector by using a number of methods. For example, a gene coding for a protein which contributes to light emission can be introduced into the DNA of a bacteriophage by using a method known to those skilled in the art.

A method for infecting a bacterium with a bacteriophage can be performed under usual infection conditions which are known in the art. Since phage infection is highly strain-specific or species-specific, the kind of phage generally determines whether a target gene (DNA) may or may not be introduced into a given bacterial cell. Some phages can infect a number of bacterial species which are of close relations. However, a majority of phages are known to infect strains of only one species. Therefore, by selecting a particular phage in view of such known infection spectra of phages, it becomes possible to specifically identify a particular strain or bacterial species which may be present in a sample.

A target bacterium is allowed to take in a vector which includes a DNA that encodes a predetermined detectable function through bacteriophage infection. By allowing the detectable function to be expressed, only the target bacterium to which the detectable function has been conferred can be selectively detected. Examples of detectable functions which are suitably used in the present invention include, without limitation, light emission, especially fluorescence. As a light-emission protein, green-fluorescent protein (GFP) or blue-fluorescent protein (BFP) can be used, for example. GFP is a particularly preferable light-emission protein for the present invention. In the case of using a light-emission protein, the external factor for inducing the detectable function may be light. However, it will be appreciated that the external factor is not limited to light. Any appropriate external factor can be used, e.g., sound, electromagnetic waves, magnetism, or pressure, depending on the detectable function used.

GFP is a light-emission protein which is produced in *Aequorea victorea*. GFP does not require any substrate to exhibit its light-emission function. A gene encoding GFP has been cloned from *Aequorea victorea*, and is known to be a protein having a molecular weight of 26,900 and consisting of 238 amino acids. In the body of a *Aequorea victorea*, green fluorescence occurs responsive to blue fluorescence, which in turn is generated from another light-emission protein called aequorin. The excitation spectrum has a peak at about 508 nm. Light emission can be attained by irradiating excitation light having an appropriate wavelength on a transformed cell, e.g., *E. coli*, or yeasts, which has been transformed so as to contain GFP.

In a gene which expresses a light-emission protein, the structural gene which encodes the light-emission protein can be a naturally occurring gene or a synthetic gene. Other light-emission proteins having similar light-emission characteristics to GFP or BFP can also be suitably employed for the present invention.

The detection of a bacterium which is caused to emit light in the aforementioned manner can be achieved by using any known means such as a photometer, a chemiluminescence reader, a scintillation counter, a luminometer, or the like. Such devices can be used to measure the amount of photons generated in a light-emission reaction. It is also possible to utilize exposure to a high-sensitivity film (e.g., "611" or "667" available from Polaroid; "hyper film MP" available from Amersham; or "X-ray film RX" available from Fuji Film) or to utilize an image analysis process employing a high-sensitivity video camera.

According to the method of the present invention, a gene encoding a desired light-emission protein is incorporated into a bacteriophage which is capable of specifically binding to a bacterium for measurement and growing therein. The phage is then mixed with the bacterium for measurement at an appropriate temperature (10° C. to 40° C.) so as to allow the phage to infect the bacterium. Thereafter, an external factor is introduced to enable detection of the bacterium for measurement.

According to the method of the present invention, not only is it possible to detect the presence or absence of a target bacterium, but it is also possible to quantitate a target bacterium based on photon amount measurements, by creating a standard curve which illustrates the relationship between bacterium concentration and the corresponding photon amounts which are detected.

Hereinafter, a method for detecting a bacterium using green-fluorescent protein (GFP) as a light-emission protein will be illustrated as a specific example of the present invention. In the following example, the FELIX01 bacteriophage was used to measure *Salmonella typhimurium* (SL1027 strain), to which the FELIX01 bacteriophage binds specifically. It will be appreciated that the following example is only of an illustrative nature, and in no way limiting the scope of the invention.

EXAMPLE

1. Medium

A nutrient medium ("nutrient broth no. 2", obtained from Yashima Pharmaceuticals) was used for cultivating bacteria. For preparing a bacteriophage solution, the nutrient medium was supplemented with 0.15 g/L of $CaCl_2$. The pH of the $CaCl_2$-supplemented broth was adjusted to 7.0. The cultivation and titration of the bacteriophage was performed on an agar medium (obtained by adding 1.5% agar to the nutrient medium).

2. Bacteria

*S. typhimurium* (SL1027 strain) was obtained from the American Type Culture Collection (ATCC).

3. Preparation of Bacteriophage Stocks

FELIX01 bacteriophage (obtained from B. A. D. Stocker, Stanford University, Stanford, Calif.) was allowed to infect *S. typhimurium* (SL1027 strain), and grow therein by cultivating the infected strain on the surface of the nutrient agar medium. The phage was harvested by flooding the surface of the medium with 0.005 M potassium phosphate buffer (pH 7.0), and collecting the buffer. The bacteria and agar debris were removed by centrifugation at 15,000×g for 30 minutes at 0° C. The bacteriophage was then concentrated in a cesium chloride-ethidium bromide density gradient (1.7 and 1.5 $g/cm^3$) by centrifugation at 62,000×g for 90 minutes at 15° C. The bacteriophage band, as visualized with ultraviolet irradiation, was removed through the side of the centrifugation polyallomar tube with a needle attached to a syringe. The CsCl was removed by overnight dialysis against 0.005 M potassium phosphate buffer (pH 7.0).

4. Preparation of FELIX01 Bacteriophage DNA

A kit designated ssPHAGE™ DNA SPIN kit (BIO 101), which is intended for the isolation of a single-stranded DNA utilizing a PEG precipitation method, was used to isolate DNA from the aforementioned bacteriophage stocks. Using the resultant single-stranded DNA as a template, a PCR reaction was carried out with a random primer, whereby double-stranded bacteriophage DNA was obtained.

5. Insertion of GFP Gene into FELIX01 Bacteriophage DNA

The FELIX01 phage DNA obtained in the aforementioned manner was digested with a restriction enzyme HindIII. A gene fragment (about 1.1 kb) of GFP (derived from *Aequorea victorea*) which had also been digested with HindIII was ligated to the FELIX01 phage DNA fragment. Thus, a recombinant phage DNA containing the GFP gene was created.

6. Production of FELIX01 Phage Particles Containing the GFP Gene

Phage particles were obtained from the aforementioned recombinant phage DNA by using an in-vitro packaging method which involves adding DNA to a bacterial virus protein mixture solution so as to obtain infectious phage particles in a test tube (Molecular Biology of the Gene, James D. Watson et al. 1988). The resultant phage particles were allowed to grow and purified in the manner described in section 3 (Preparation of bacteriophage stocks). Portions of the bacteriophage particles which were not going to be used immediately were stored as an aseptic lysate in a test tube disposed above liquid nitrogen and maintained at a low temperature.

7. Infection of *S. typhimurium* (SL1027 Strain) with the Phage Particles

*S. typhimurium* (SL1027 strain) was infected with FELIX01 phage containing the GFP gene in a nutrient medium. Specifically, 10 ml of medium was placed in a 125 ml Erlenmeyer flask. This medium was inoculated with *S. typhimurium* (SL1027 strain), and then incubated so that the bacteria grew to about $10^4$ to $10^6$ cells/ml with shaking the flask in a water bath at about 37° C. Then, in the same flask, the phage particles were added to a concentration of about $3 \times 10^8$ PFU/ml. As a control, a flask not containing any *S. typhimurium* (SL1027 strain) was subjected to the same procedure.

These flasks were incubated by shaking at 200 rpm in a water bath (equipped with a shaker) at about 37° C. Two hours later, the fluorescence of the broth in the flasks was measured.

8. Measurement of Light Emission

A 50 μl sample was collected from each broth, which was diluted stepwise to cell concentrations ranging from about 1 to about $10^3$ cells/ml and placed in polystyrene cuvettes. The cuvettes were placed in a temperature-controlled cuvette holder which was provided in the measurement apparatus, and subjected to a spectrophotometric measurement. By using an SLM Aminco Bowman AB2 fluorescence photometer (Fisher; Pittsburgh, Pa.; catalog #14385991F), fluorescence in the range of about 490 to about 520 nm was measured with an excitation wavelength of about 396 nm.

The fluorescence was measured for both the flask containing *S. typhimurium* (SL1027 strain) and the flask not containing *S. typhimurium* (SL1027 strain). The measurement value obtained for the flask not containing *S. typhimurium* (SL1027 strain) was used as a background, which was subtracted from the measurement value obtained for the flask containing the cultivated sample. The resultant values representing light emission amounts were plotted against the concentration of *S. typhimurium* (SL1027 strain) (shown in the figure).

Thus, according to the present invention, a highly-sensitive and highly-reliable method for detecting or identifying bacteria is provided.

By utilizing the method of the present invention, it is possible to detect and measure bacteria in a quick and specific manner, without requiring complicated processes.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for determining the presence or absence of a bacterium in a sample, comprising the steps of:

introducing into a bacteriophage a 1.1 kb HindIII polynucleotide fragment encoding a green-fluorescent protein (GFP) derived from *Aequorea victorea* to produce a transformed bacteriophage;

contacting the sample with the transformed bacteriophage;

allowing the transformed bacteriophage to bind to a bacterium which is present in the sample, the transformed bacteriophage being capable of specifically binding to the bacterium and growing in the bacterium;

growing the transformed bacteriophage in the bacterium up to a level below where destruction of the bacterial cell occurs and expressing the green-fluorescent protein in the bacterial cell during which the cell number of the bacterium does not increase substantially;

providing light of a first wavelength from outside the sample, whereby the actually-present bacterium emits light of a second wavelength;

measuring the light of the second wavelength emitted by the light-emitting protein in the bacteria in the sample; and determining the presence or absence of the bacterium in the sample from the amount of light emitted compared to a sample containing none of the bacterium;

wherein the bacterium is selected from the group consisting of Salmonella, Pseudomonas and *E. coli*;

and wherein if the bacterium is suspected of being Salmonella, the bacteriophage is FELIX01;

and wherein if the bacterium is suspected of being Pseudomonas, the bacteriophage is φ6 or PM2;

and wherein if the bacterium is suspected of being *E. coli*, the bacteriophage is selected from the group consisting of T4, P2, T2, T7, λ, φX174 and MS2.

2. A method according to claim 1, whereby the bacterium is Salmonella and the bacteriophage is FELIX01.

3. A method according to claim 1, whereby the bacterium is Pseudomonas and the bacteriophage is φ6 or PM2.

4. A method according to claim 1, whereby the bacterium is *E. coli* and the bacteriophage is selected form a group consisting of T4, P2, T2, T7, λ, φX174 and MS2.

5. A method according to claim 1, whereby the sample is an environmental sample, a food sample or a medical sample.

* * * * *

UNITED STATES PATENT AND TRADEMARK OFFICE
CERTIFICATE OF CORRECTION

PATENT NO. : 6,555,312 B1  
DATED : April 29, 2003  
INVENTOR(S) : Nakayama

It is certified that error appears in the above-identified patent and that said Letters Patent is hereby corrected as shown below:

<u>Title page, Item [54] and Column 1, line 2,</u>  
Replace "BACTERIAPHAGE" with -- BACTERIOPHAGE --.

<u>Column 8,</u>  
Line 51, replace "form" with -- from --.

Signed and Sealed this

Twenty-second Day of July, 2003

JAMES E. ROGAN  
*Director of the United States Patent and Trademark Office*